United States Patent [19]
Herpst et al.

[11] Patent Number: 6,146,900
[45] Date of Patent: Nov. 14, 2000

[54] METHOD AND APPARATUS FOR THE PRODUCTION OF FILMS

[75] Inventors: Robert D. Herpst, 11 Trotters La., Mahwah, N.J. 07430; Kenneth B. Cuthbert, Quakertown, Pa.

[73] Assignee: Robert D. Herpst, Garfield, N.J.

[21] Appl. No.: 09/179,672

[22] Filed: Oct. 27, 1998

Related U.S. Application Data

[60] Provisional application No. 60/063,575, Oct. 30, 1997.
[51] Int. Cl.⁷ ............................. G01N 21/03; B29C 49/08
[52] U.S. Cl. ........................ 436/165; 264/291; 264/292; 446/15
[58] Field of Search ..................................... 264/291, 292; 359/389; 446/15; 436/165

[56] References Cited

U.S. PATENT DOCUMENTS

| | | |
|---|---|---|
| 3,950,887 | 4/1976 | Kort . |
| 3,961,122 | 6/1976 | Gaines, Jr. et al. . |
| 4,279,855 | 7/1981 | Ward, III ................................. 264/298 |
| 4,374,891 | 2/1983 | Ward, III . |
| 4,790,787 | 12/1988 | Rector . |
| 5,345,333 | 9/1994 | Greenberg ............................... 359/389 |
| 5,512,229 | 4/1996 | Bosse et al. ............................. 264/161 |

FOREIGN PATENT DOCUMENTS

| | | |
|---|---|---|
| 2262243 | 6/1993 | United Kingdom . |
| 2315028 | 1/1998 | United Kingdom . |
| WO 86/05408 | 9/1986 | WIPO . |
| WO 92/19342 | 11/1992 | WIPO . |

*Primary Examiner*—Jill Warden
*Assistant Examiner*—Dwayne K. Handy
*Attorney, Agent, or Firm*—Roger M. Rathbun

[57] ABSTRACT

Methods and apparatus for forming a film of a liquid material and for employing the film as a test sample for determining properties of the material in a suitable analytical instrument such as a spectrophotometer.

18 Claims, 8 Drawing Sheets

METHOD AND APPARATUS FOR THE PRODUCTION OF FILMS

This application claims benefit of provisional application Ser. No. 60/063,575 Oct. 30, 1997.

FIELD OF THE INVENTION

The present invention is directed to a method and apparatus for the production of films, especially thin films from a liquid by the deposition of the liquid onto a frame comprised of at least three sides, at least one of the sides being moveable and the use of surface tension and capillary action to draw the liquid over the frame to form a film. The films produced can be used, for example, for analysis by spectroscopy.

BACKGROUND OF THE INVENTION

According to Beer's Law, absorbance increases as the pathlength or thickness of a sample increases. Many samples for which the analytical technique of preference is infrared spectroscopy, such as polymers, solvents and lubricants, are inherently highly absorbing. It is difficult to obtain useful information about these samples by spectroscopic analysis if the apices of the absorbance peaks generated by the spectrophotometer of are too high, i.e. the absorbance peaks will tend to exceed the "Y" axis or ordinate scale of the spectrophotometer. When the apex of an absorbance peak exceeds the "Y" axis of the analyzer, it is impossible to determine the intensity of the peak with acceptable accuracy. In addition, the absorbance peaks of such samples tend to obscure each other if the absorbance peaks are too intense, as is often the case with relatively thick samples.

Accordingly, it is difficult to compare the spectra of samples that have obscured absorbance peaks with spectra of other samples that do not have the same peaks obscured. It is also difficult to compare spectra with peaks that are obscured by other more intense peaks with spectra of samples made from films that show more absorbance peaks. In addition, the optical materials between which samples are deposited produce interference fringes and can absorb energy both of which can obscure absorbance peaks. Thus, the spectrometric analysis of films is rendered problematical in part because the absorbance measurements can be obscured causing difficulty in reading and comparing absorbance peaks.

It is known that more readable absorbance patterns can be obtained if the thickness of the film is reduced. There are techniques available for producing samples from liquids and viscous materials. These include transmission sampling using liquid cells, pressing thin films from polymers using polished platens and laboratory presses, and internal reflection and specular reflection spectroscopy. All of these techniques have certain limitations in providing suitable samples for analysis especially spectroscopic analysis.

Transmission sampling using cells requires that the sample be injected into the cell with a syringe or under pressure, which makes filling of the cell somewhat cumbersome. The technique is not practical for highly viscous samples and for samples which adversely affect the cell such as adhesives. Using presses and dies is cumbersome and is not practical for liquids. Internal reflection and specular sampling produces spectra which are not directly comparable with transmission spectra and conversion of the results is cumbersome and error prone. The internal reflection technique cannot be used to produce thin films as there is no practical means of accurately controlling sample thickness, and the optics obscure the detail of spectra in the 600 to 400 cm-1 range.

In other fields, such as cytology, thin samples are desirable because if the specimen comprises several layers of cells (a relatively thick sample) it is difficult to distinguish one layer from another when one layer of cells is overlaid with another layer of cells. Thin films are also useful for testing the physical properties of samples, such as tensile strength testing.

Liquid samples have traditionally been tested in spectrophotometers by placing the sample in a vessel also known as a cell. Cells are comprised of sealed cavities bounded by a pair of windows made from optical materials which, when mounted in the beam of energy (e.g. light) emitted by the energy source of the spectrophotometer, will not absorb the energy that passes through them. The cells are typically mounted vertically in the sample compartment of the spectrophotometer. Liquid cells used in infrared spectrophotometers are normally filled with a syringe, as cell volumes and pathlengths (the space between the windows) tend to be small.

Another spectroscopic sampling technique is known as the attenuated total reflectance (ATR) sampling technique (also known as multiple internal reflection (MIR) sampling). In this technique, the sample is placed against the planar surface of a prism made from an optical material with a high refractive index, and the beam of energy of the spectrophotometer is directed through the end of the prism which is at an angle (usually 30 to 60 degrees). The beam bounces one or more times against the sample.

This technique was originally practiced with accessories used in the vertical position, but it was impractical to use it with liquids because there was no means of containing the liquid sample in a manner that would keep the sample in contact with the face of the prism. In about 1980, an improvement to the ATR technique was introduced to enable analysis of the sample in the horizontal position. This innovation allowed the use of ATR accessories with liquids and it has become popular because the sample can simply be poured into the accessory and then dumped out after the sample has been tested in a spectrophotometer.

ATR techniques require an optical bench comprised of mirrors to direct the beam from the energy source through the prism and then to the detector of the instrument, whereas a cell sits directly in the beam of the instrument and the spectrophotometer beam passes in a straight line from the energy source through the sample and on to the detector of the instrument. Both ATR spectroscopy and transmission spectroscopy using a cell require the use of some optical material as a substrate (the prism) or to hold the sample (transmission windows).

It would be an advance in the art of producing samples for analysis especially by infrared spectroscopy to be able to produce films that are relatively thin from highly absorbing samples that can be analyzed in the transmission mode without the need for cumbersome techniques such as liquid cells and polymer film pressing and which eliminate some of the inherent shortcomings of simpler techniques such as internal reflection sampling. It would be an advance in the art of producing tissue and cell samples to be able to produce controlled thickness thin films which approach the thickness of a single layer of cells.

SUMMARY OF INVENTION

The present invention is directed in part to a method and apparatus for forming a film, preferably a thin film from a liquid sample using a frame with a variable geometry. The sample is deposited on the frame, defining a film-forming area, at a relatively narrow point on the frame (an apex or neck) and then drawn across the frame within the film-forming area so that all sides of the frame are contacted with the liquid sample.

The material of the sample is highly attracted to the frame. In some cases, capillary action enables the sample to be drawn up along the frame while surface tension holds the film together within the film-forming area. The frame may be located in a sample reservoir or well that will allow liquid to be drawn from the well and along the frame until the sample is exhausted, which results in long lasting liquid phase films.

The frame can be made both narrow and small to accommodate low viscosity samples and can be widened and extended for higher viscosity samples. Further, film size and/or thickness can be regulated by increasing the size of the frame or by rotating the frame using centrifugal force. Liquid films can be sampled by transmission without the need for a substrate. These films last considerably longer if they are left in the horizontal position. In one aspect of the invention, the film may be analyzed in the horizontal position in which a horizontal beam of energy (e.g. light) of a spectrophotometer or other energy source is directed through a transmissive sample or substrate which is positioned horizontally and outside of the path of such beam of energy using an optical bench or mirrors.

More specifically, in one aspect of the present invention, there is provided a method of forming a film from a sample of a liquid comprising:

a) applying a liquid onto a frame comprising at least three sides with at least one of the sides being moveable;

b) contacting the liquid with said moveable side, said moveable side being in contact with at least two of the sides of the frame; and c) moving the moveable side in a manner sufficient to draw the liquid between the sides in contact with the moveable side within a film-forming area to form said film.

There is also provided in accordance with the present invention a method of detecting the absorbance peaks created by a material or the molecular or chemical structure of a material when exposed to an energy source and an apparatus for forming a transmissive film for analysis thereof comprising:

a) a frame comprising at least three sides, at least one of the sides being moveable; and b) said moveable side being in contact with at least two of the sides; wherein when the frame is in contact with said liquid sample the moveable side is moveable along at least two sides of the frame to draw the liquid between said at least two sides in a film-forming area to form said film.

In another aspect of the invention, there is provided a method of detecting the absorbance peaks created by a material or the molecular or chemical structure thereof when the material is exposed to an energy source wherein the frame is mounted horizontally in an apparatus containing an energy source using an optical bench comprised of mirrors.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

The present invention is generally directed to forming a film especially a thin film from a liquid or viscous sample that is intended to be transmissive. The film can be used for analysis by spectroscopy, for physical testing of material properties, or for viewing any sample wherein the creation of the film sample is desirable, such as, but not limited to, cytological testing of human or animal tissue.

The film has a thickness which will vary but it is preferred that the film be sufficiently thin so that the passing of a beam of energy (e.g. light) into contact with the film will produce absorbance peaks which are distinct for the principal absorbance wavelengths of the sample material. In accordance with the present invention, a liquid sample of material to be tested is formed into a suitable film and then used in an analytical instrument or other instrument such as a microscope or an infrared spectrophotometer wherein the transmissive nature of the film is useful for facilitating analysis within the instrument, such as the study of absorbance peaks in the field of spectroscopy.

Figure 1:
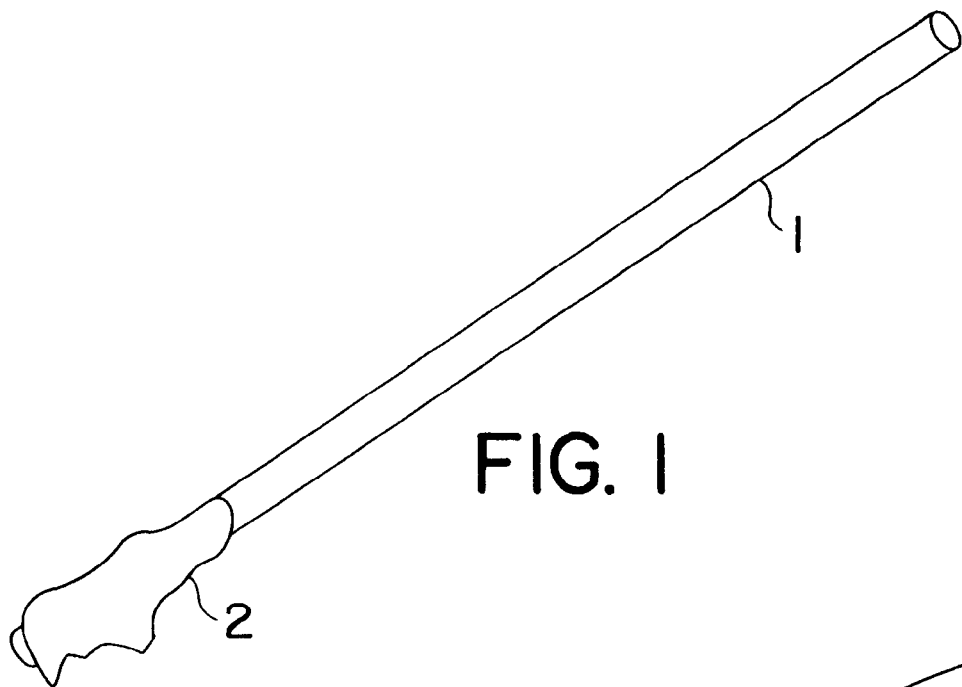
FIG. 1 is a perspective view of a liquid sample adhering to a glass wand.
Figure 2:
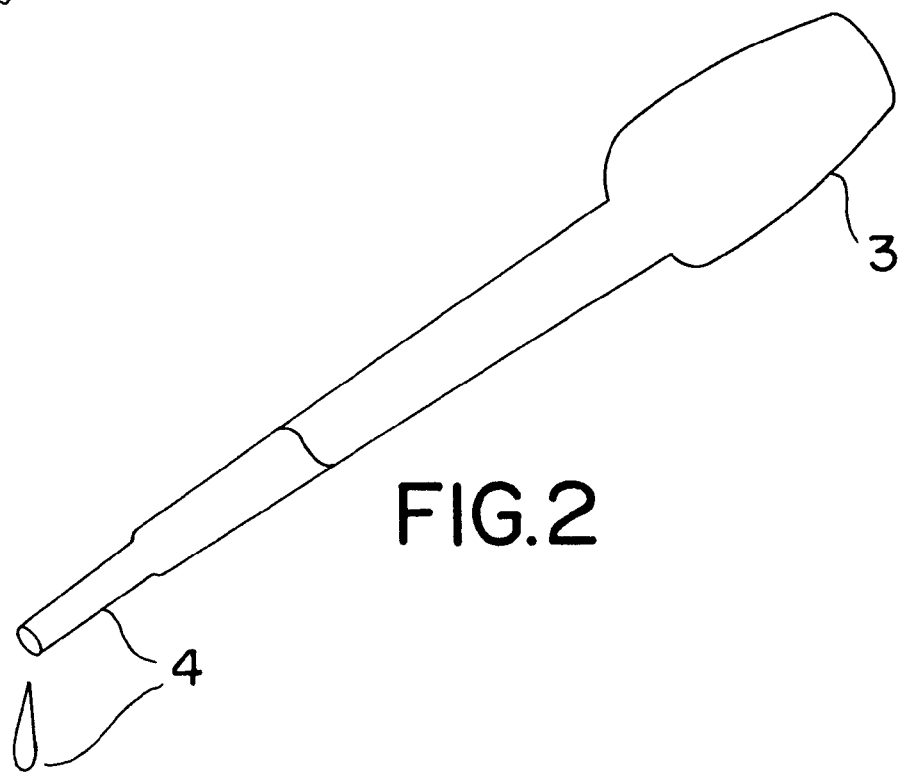
FIG. 2 is a perspective view of a liquid sample suctioned into a pipette.

Referring to FIGS. 1 and 2, a liquid or viscous sample 2 may be collected by contacting the same with a wand or rod. The liquid adheres to the wand 1 by adhesion. The wand can be made of any material which enables adhesion to occur and does not adversely affect the liquid sample. Examples of such materials include glass, plastic, ceramic, wood and metals. Glass is the preferred material for the wand. Alternatively, the sample 4 may be drawn into a pipette 3 as shown specifically in FIG. 2. It is understood that any means of collecting the sample known in the art, such as by adhesion to another carrier substance or by suction or the like may be used.

The sample is contacted with a film-forming device defining a film-forming area in the form of a frame having at least three sides defining the film-forming area. The frame is comprised of at least three opposed sides at least one of which is moveable. The moveable side traverses at least two of the sides so that it spans the film-forming area. In this way, as explained hereinafter, the moveable side draws the liquid sample between the traversed sides of the frame over the film-forming area to form the film which is to be tested or analyzed. The frame which may typically be constructed of wood, metal, wire plastic and the like is generally comprised of at least three sides, but may include several sides in the form of a polygon or even in the form of an oval or circle. What is essential for the proper employment of the frame is that there be a film-forming area lying between the borders of the frame which enables a liquid sample to contact the sides of the frame as the sample is drawn over the film-forming area to form a film.

It will also be understood that in accordance with the invention, the film-forming device may employ a wide range of geometries and modes of operation to define the film-forming area. By way of example, the film-forming device may employ a mechanism similar in operation to a camera shutter wherein all sides of the "frame" are moveable to enlarge a centrally located aperture where the liquid sample is initially placed. As long as all of the sides of the frame are contiguous and lie on the same plane, a suitable film can be formed in accordance with the invention.

Figure 3:
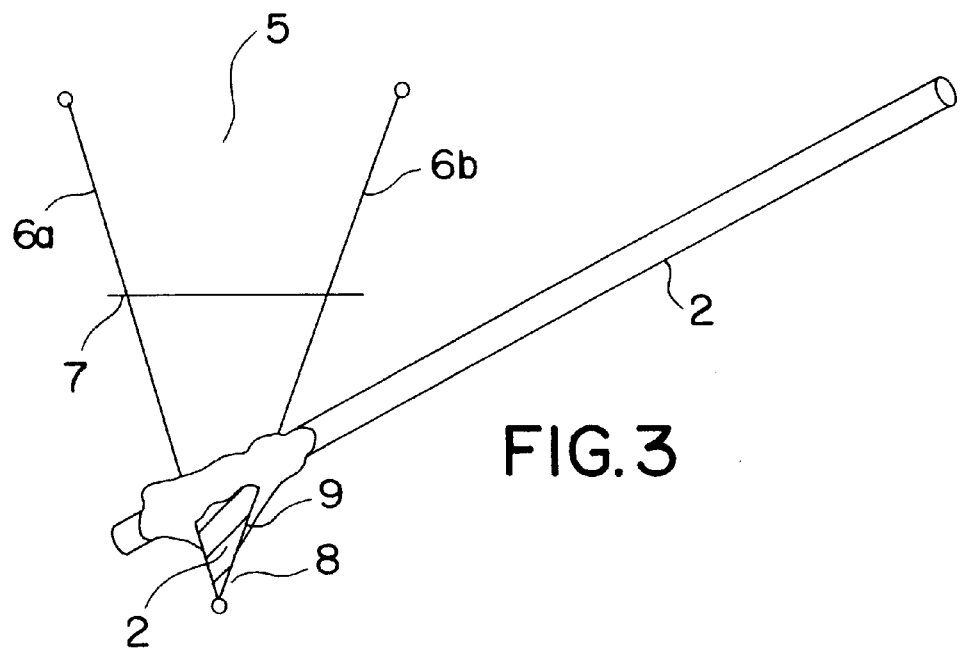
FIG. 3 is a schematic view of a liquid sample being transferred from a glass wand to a frame.
Figure 4:
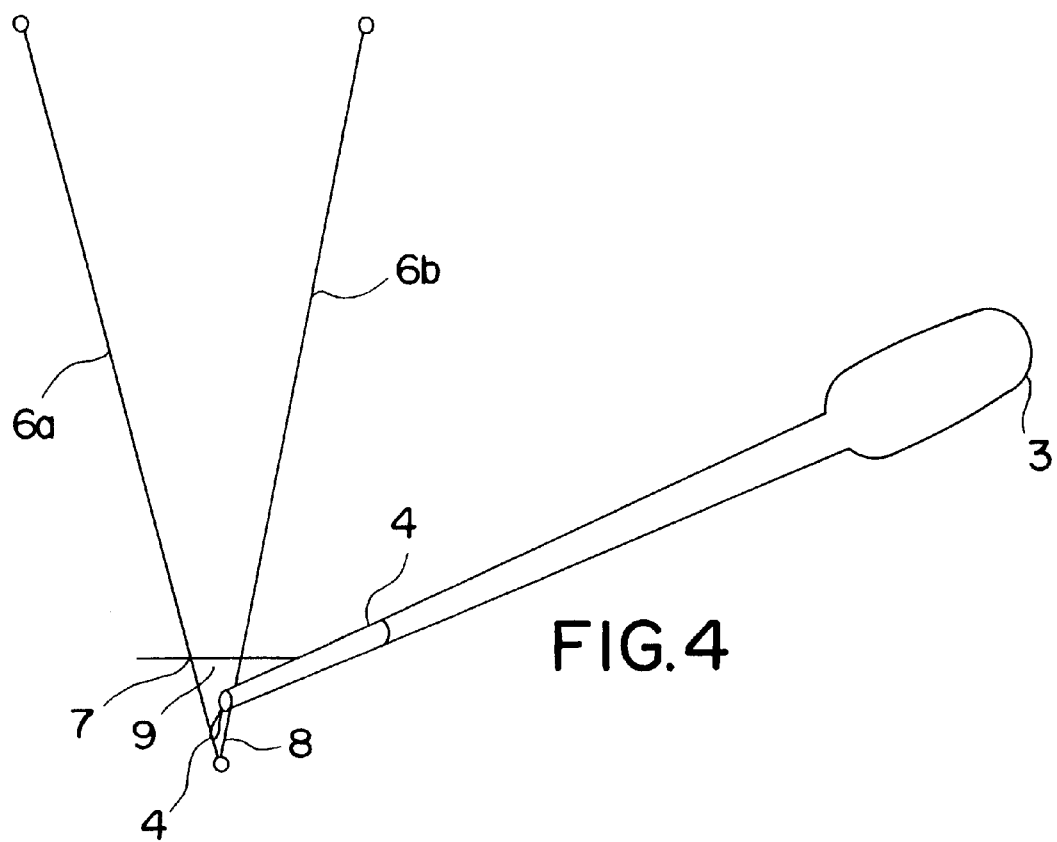
FIG. 4 is a schematic view similar to FIG. 3 in which a liquid sample is transferred from a pipette to a frame.

Referring to FIGS. 3 and 4 there are shown embodiments of the invention in which an embodiment of a frame useful in the present invention has a pair of opposed, spaced apart sides which converge at an apex. For purposes of these embodiments, the frame, which forms a triangle with a moveable side (e.g. a rod), will be referred to herein as a triangular frame as explained in detail hereinafter.

Figure 5:
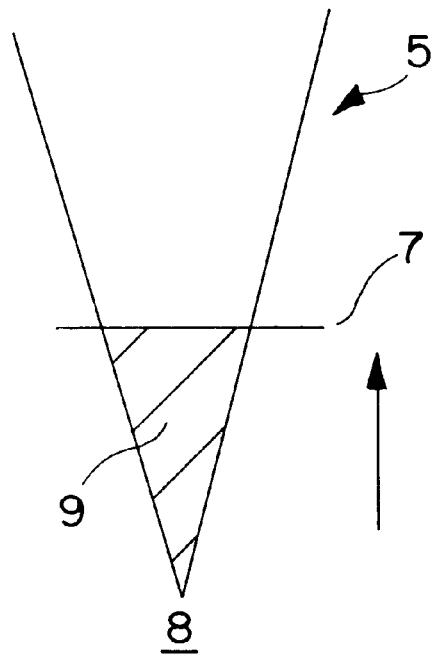
FIG. 5 is a plan view of a film formed in accordance with the present invention adhering to a frame.
Figure 6A:
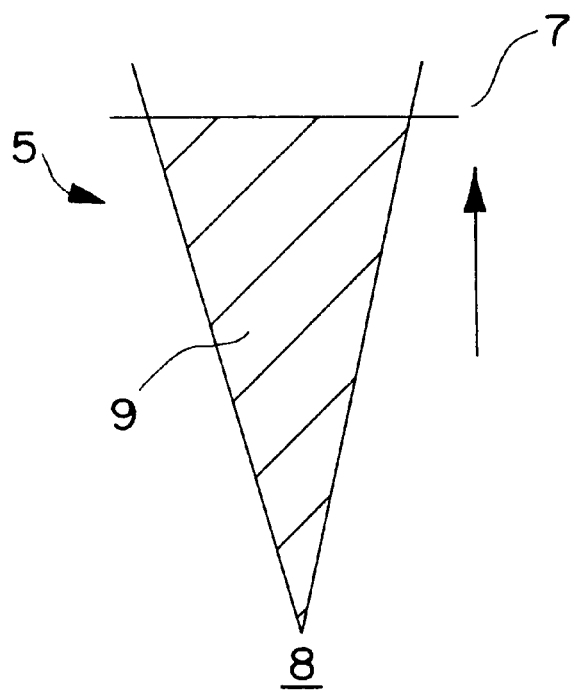
FIG. 6A is a plan view similar to FIG. 5 in which the film is stretched over the frame by moving the rod to increase the area defined by the frame.

As shown in FIG. 3, the triangular frame shown generally by the numeral 5 comprises opposed, spaced apart sides 6a and 6b and a moveable rod 7 transversing the sides 6a, 6b which together define the triangular shape and a film-forming area 9. The sides 6a and 6b converge at an apex 8 which will first contact the liquid sample. The sample is deposited at the apex 8 of the triangular frame 5 by use of a glass wand 1 (as specifically shown in FIG. 3) or by a pipette as shown in FIG. 4. The sample is then drawn along the sides 6a, 6b of the triangle 5 by the rod 7 which moves along the sides 6a, 6b of the triangular frame as shown in FIGS. 5 and 6A. The sample 2 transfers to and adheres to the sides 6a, 6b and, eventually transfers to all sides of the frame to form a film within the film-forming area 9 when the rod 7 reaches the position shown in FIG. 6A. The surface tension of the sample as it is being drawn along the sides 6a and 6b by the rod 7 should not be so high as to cause the resulting film within the film-forming area 9 to break. If the film breaks, the rod 7 is moved closer to the apex 8 of the triangular frame or the sides 6a, 6b are moved closer together.

Once the film within the film-forming area 9 has adhered to all sides of the frame 5, the rod 7 may be moved further away from the apex 8 to make the film-forming area 9 larger and the film even thinner to thereby expand the film-forming area 9. Movement of the rod 7 can therefore control the size of the film-forming area 9 and/or the thickness of the film within the limits of the adhesion and surface tension characteristics of the material from which the film is made.

FIG. 4 shows a preferred embodiment of the invention in which the sample 4 is transferred by means of a pipette 3.

The sample 4 is applied as a droplet at the apex 8 of the triangular frame and then the film within the film-forming area 9 is formed by contacting the rod 7 with the sample 4 then drawing the rod 7 away from the apex 8 until the desired film size and thickness are achieved.

FIGS. 5 and 6A show the film-forming area 9 being enlarged by drawing the rod 7 of the frame 5 away from the apex 8. As the rod 7 is moved further away from the apex 8 the resulting film within the expanding film-forming area 9 will become larger (i.e. increase in surface area) and thus thinner unless and until the point is reached when the sample has been subjected to more surface tension than the film can withstand, which will break the film.

Figure 6B:
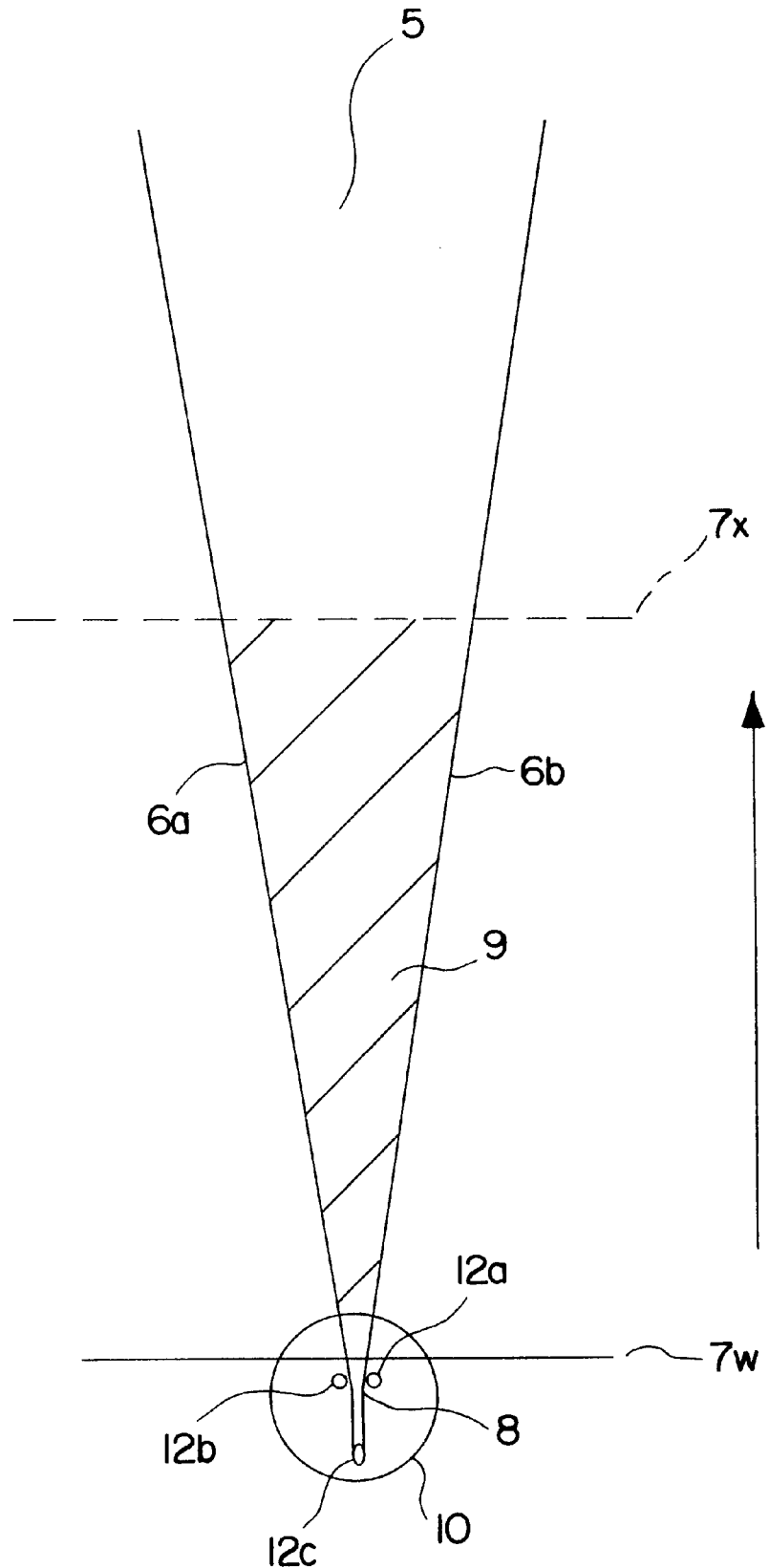
FIG. 6B is a perspective view showing a liquid sample deposited in a concave well and the apex of a frame placed in contact with the well.

FIG. 6B shows an embodiment of the invention employing a well 10 at the apex 8 of the triangular frame 5 where the sides 6a, 6b forming the apex 8 converge by the application of opposed pins 12a, 12b. The sides are connected to a third pin 12c beyond the apex 8. The sample is deposited in the well 10 and the film-forming area 9 is formed by contacting the moveable rod 7 at the apex 8 with the sides 6a, 6b and drawing the rod 7 from an initial position indicated at 7w along the sides towards the wider part of the frame 5, at a position 7x where the desired area and thickness of the film within the film-forming area 9 are achieved. The strong adherence of the sample at the apex 8 formed by the sides 6a, 6b of the frame 5 causes the sample to be drawn up from the well 10 towards the rod 7 at the wider portion of the frame (e.g. when the rod 7 is at a position 7x) so that when the sample is in liquid phase it replenishes itself until the well 10 is empty.

When the sample remains in the liquid phase, the well 10 will feed liquid to the sides 6a, 6b of the frame 5 which will continue to pull sample from the well by capillary action even after the rod 7 ceases to be moved. This results in an extremely long lasting film in the liquid phase, as the well 10 replenishes evaporating sample and the surface tension on the film does not increase to the level at which the film will break as rapidly as would be the case if there was no well. Such films will last for several minutes or more in the horizontal position even if the film does not reach a viscoelastic state.

For convenience of analysis, it would be preferable to have a film last as long as possible so that the analyst has sufficient time to set up the sampling accessory in the analytical instrument such as a spectrophotometer and to run the sample or to do such other tests as may be desired. For example, a sample composed of xylene will last for up to 30 minutes in the horizontal position whereas the sample may last only a few minutes or less in the vertical position. Set up can, in some cases, take longer than the film will last when it is in the vertical position. Accordingly, the present invention enables the production of films, preferably in the horizontal position, to facilitate testing thereof.

Figure 10:
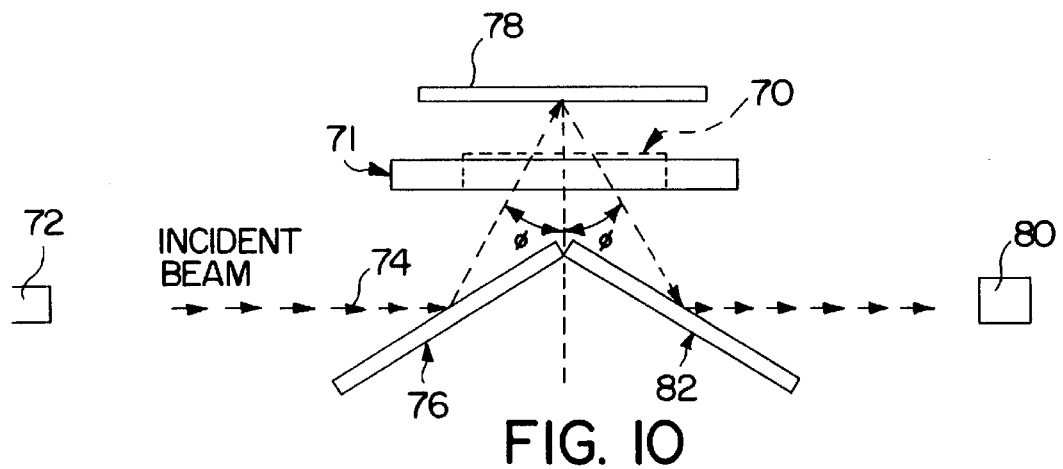
FIG. 10 is a schematic view of an embodiment of the invention for spectroscopic analysis of a material lying in a horizontal position of a spectrophotometric instrument.

Referring to FIG. 10, there is shown an embodiment of the invention in which a sample in the form of a thin film may be analyzed in a horizontal position. As shown in FIG. 10, the film 70 formed by a film forming device 71 as previously described, is placed in the horizontal position within an instrument having an energy or light source 72. The beam of incident beam energy or light 74 is also horizontal. The incident beam is directed to the thin film sample 70 by a mirror 76 that is placed at an angle φ (e.g. about 30°) and then back through the sample 70 by a second mirror 78 which returns the beam to the same level as the incident beam so that it can be directed to a detector 80. In this preferred embodiment of the invention, the energy beam passes through the sample twice, which results in more intense absorbance peaks than if the beam only passed through the sample once.

Figure 11:
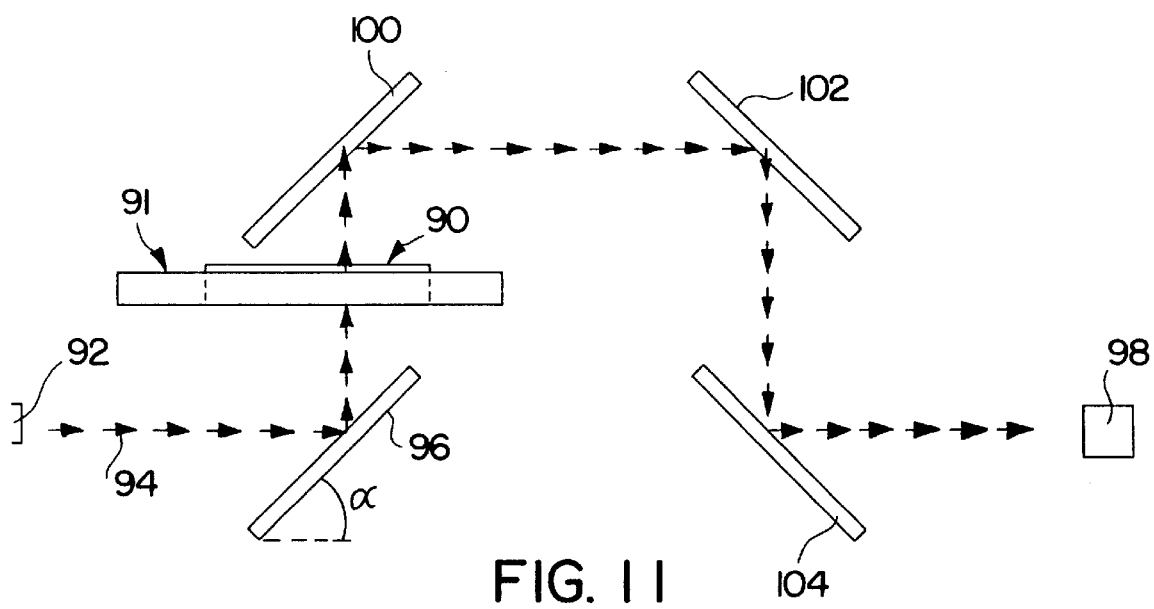
FIG. 11 is a schematic view of another embodiment of the invention for spectroscopic analysis of a material lying in a horizontal position of a spectrophotometric instrument.

In a further embodiment of the invention, the energy beam passes through the horizontally positioned film sample only once. Referring to FIG. 11, the film 90 formed by a film forming device 91 as previously described, is placed in the horizontal position within an instrument having an energy or light source 92. The beam of incident beam energy or light 94 is also horizontal. The incident beam is directed to the sample 90 by a mirror 96 that is placed at an angle α (e.g. about 45°) and then back to the level of the incident beam 94 and on to a detector 98 by a second mirror 100 and a third mirror 102 which returns the beam to same level as the incident beam. A fourth mirror 104 then directs the beam of energy to the detector 98. In this preferred embodiment of the invention, the energy beam passes through the sample only once, which results in less intense absorbance peaks than would be the case if the beam passed through the sample twice as was shown in the embodiment shown in FIG. 10.

It is understood that first surface mirrors should be used as shown in FIGS. 10 and 11 so that no spurious absorbances are detected from the non reflective material comprising the mirror. It is also understood that the instrument in which the horizontal sample film is placed may be an FTIR microscope as well as a spectrophotometer or other type of suitable analyzer.

Figure 7:
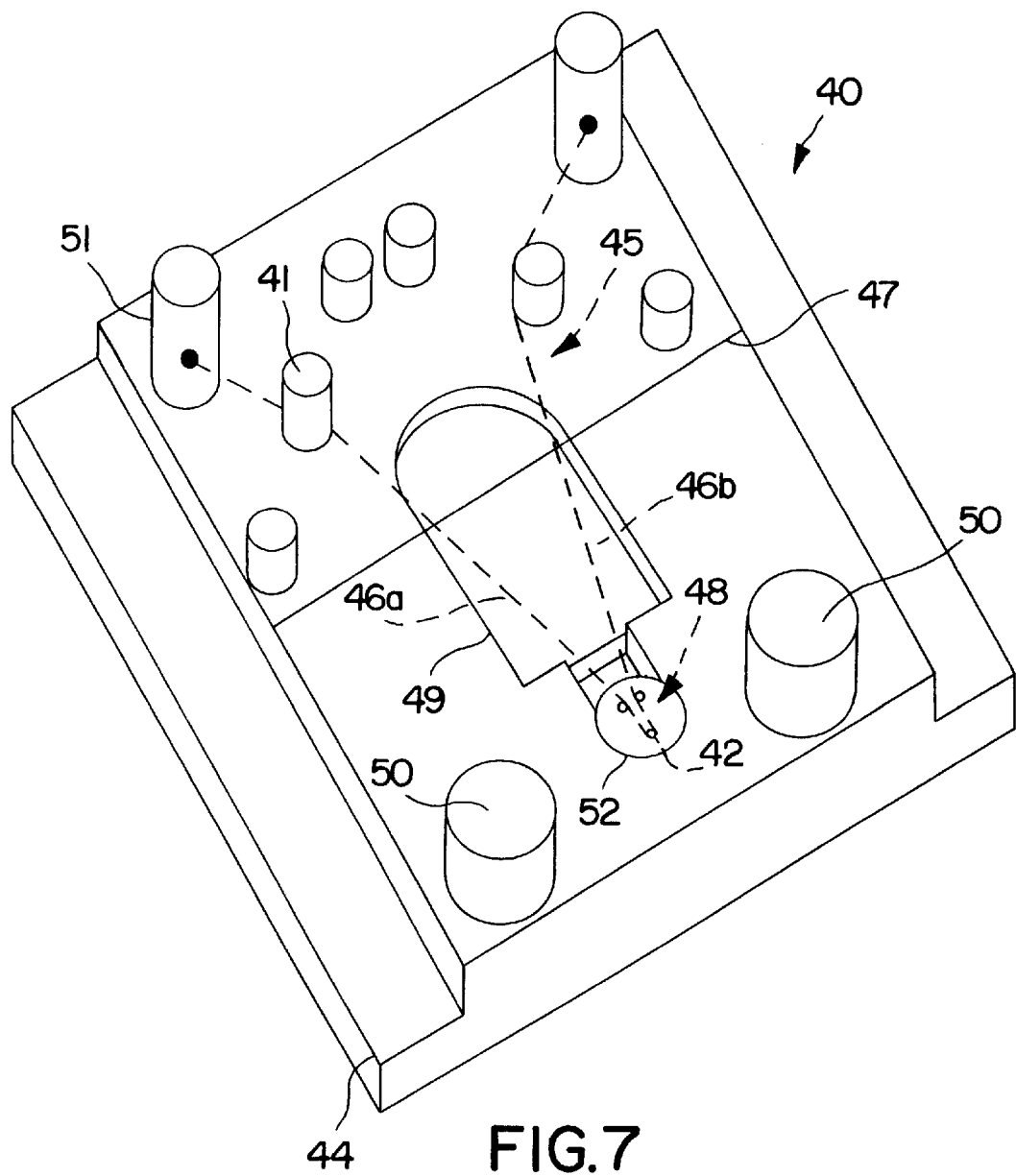
FIG. 7 is a perspective view of a preferred embodiment of an apparatus used to form a film in accordance with the present invention.

FIG. 7 shows a preferred embodiment of the film-forming device of the invention employing a frame made from wires with the film being formed in the film-forming area between the spaced apart wire sides. The frame is contained within a portable device for facilitating conducting of the film forming process in proximity to the location of the analysis equipment (e.g. a spectrophotometer). Referring to FIG. 7 there is provided a device 40 including a backplate 44 and a plurality of pins 41 for positioning wires or filaments that form the sides 46a, 46b of the triangular frame 45. The frame 45 can be made wider or narrower by moving the location of the wires to appropriate pins 41 that will make a suitable frame width. A pin 42 at the apex 48 of the triangular frame 45 in proximity to the well 52 containing the liquid sample material is used to enable the wire to be stretched. At one end of the device 40 there are two knurled screws or nuts 51 for clamping and stretching the wires 46a,b after the frame width is properly adjusted using the location pins 41. The triangular frame 45 is mounted on the backplate 44 of the type normally used in an infrared spectrophotometer to mount slide mounted accessories in the vertical position. The backplate 44 can also be used when the invention is used as a microscope stage and can be used in the horizontal position. The backplate 44 contains a hole 49 through which energy (e.g. light) from the spectrophotometer or other analyzer or microscope can pass and then transmit through the sample film. When used in the vertical position the sample film is manipulated by moving the backplate 44 up or down in the slide mount of the instrument and then securing the backplate 44 in the desired position using one or more knurled screws or thumb screws 50 which position the slide mount assembly within the beam of energy along the Y axis. In the horizontal position, the backplate can simply be moved as desired. When the film sample is positioned in the horizontal position in a spectrophotometer or other energy beam generating instrument that directs the energy beam horizontally, it is necessary to use an optical bench as previously described in connection with FIGS. 10 and 11 to direct the energy beam through the film.

To reproducibly control the thickness of the film, the invention may be rotated by a device that can precisely and reproducibly control the speed of rotation and the duration of the rotation cycle.

Figure 8:
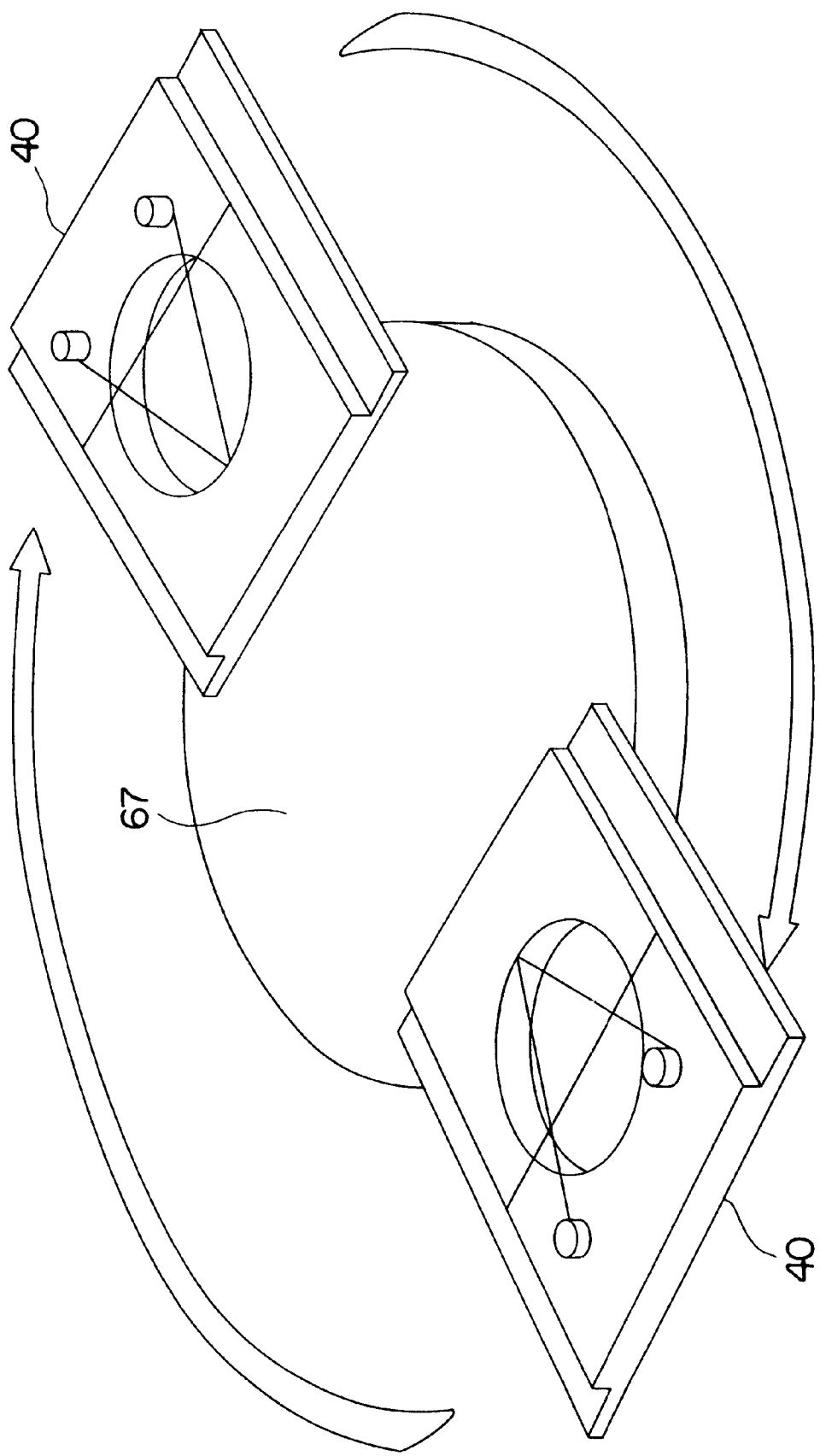
FIG. 8 shows a perspective view of a frame of the present invention being rotated so that centrifugal force is applied to the film.

As shown in FIG. 8, two devices 40 shown in FIG. 7 are attached to a rotating substrate 67 to control the thickness of the film. In this mode, the excess liquid is thrown off of the frame and the film becomes thinner. By replicating the speed of rotation and the duration of rotation, the film thickness can be duplicated with consistency from sample to sample. It will be understood that a single device 40 could also be mounted directly over the axis of the rotating substrate 67, so as to employ centrifugal and centripetal forces and to apply those forces to the film on the frame with radial symmetry.

Figure 9A:
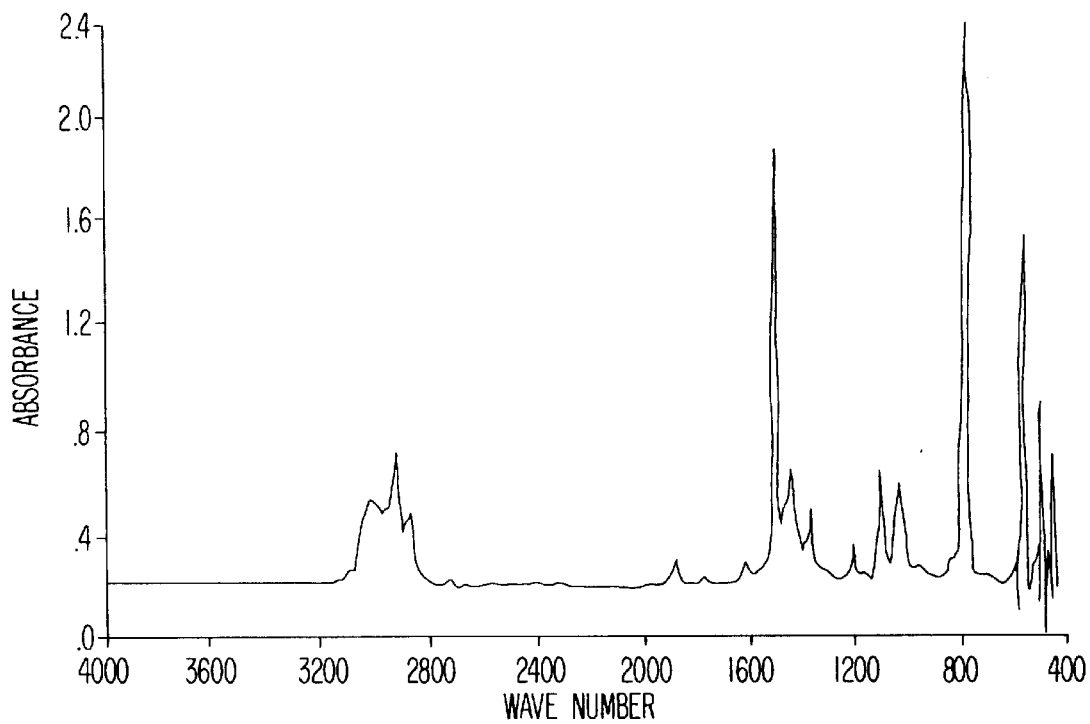
FIG. 9A is a spectra of xylene taken from conventional horizontal ATR.
Figure 9B:
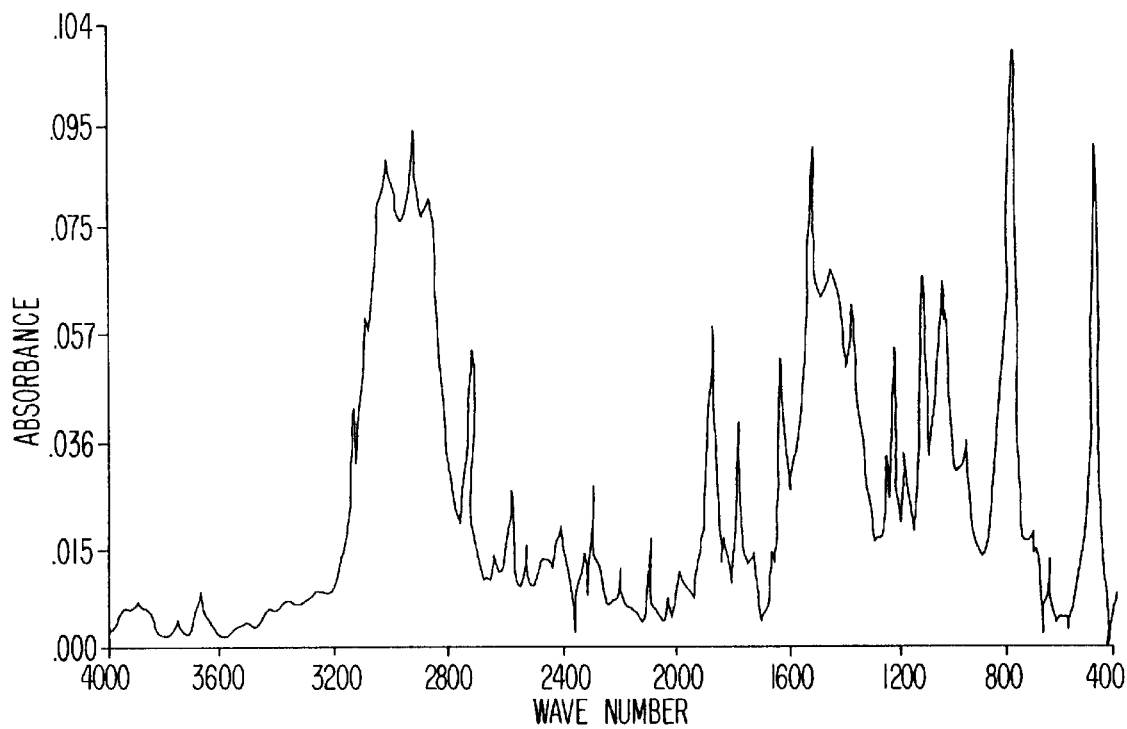
FIG. 9B is a spectra of xylene obtained in accordance with an embodiment of the present invention.

FIGS. 9A and 9B show comparative spectra produced on an FTIR spectrophotometer of films comprised of xylene made in accordance with a preferred embodiment of the invention as previously described (FIG. 9B) and on a prior art ATR (FIG. 9A). The height and clarity of the absorbance peaks of the film produced in accordance with a preferred embodiment of the invention as shown in FIG. 9B is the result of a considerably thinner film than the film produced in the prior art ATR. Furthermore, the HATR optic distorts the spectra in the 600 to 400 cm-1 range and there is very little detail that can be observed of absorbance peaks range from 2200 to 1600 cm-1 because of interference fringes, while other interference fringes create the illusion of absorbance peaks that do not exist. However, the spectrum made from the thin film made with a preferred embodiment of the invention shows many absorbance peaks with very fine detail in these same regions, which exhibits the infinitely finer sensitivity of the method and apparatus.

What is claimed:

1. A method for forming a film from a sample of liquid in the absence of a substrate, said method comprising:
    a) applying said liquid into a frame comprising at least three sides with at least one of the sides being moveable into contact with the sample of liquid;
    b) contacting the liquid with said moveable side, said moveable side being in contact with at least two of the sides of the frame to thereby define a film-forming area;
    c) moving the moveable side in a manner sufficient to draw the liquid between the sides in contact with the moveable side within the film-forming area to form said film in said film-forming area.

2. The method of claim 1 further comprising controlling the size of said film-forming area.

3. The method of claim 1 further comprising controlling the thickness of said film.

4. The method of claim 2 comprising adjusting the distance between the sides of the frame.

5. The method of claim 3 comprising rotating the frame at a sufficient rate of speed to remove excess liquid from the frame.

6. The method of claim 1 wherein the frame comprises two spaced apart sides which converge at an apex, said method comprising contacting said apex with the liquid and drawing the liquid with the moveable side from said apex.

7. The method of claim 1 comprising moving a plurality of the sides of the frame to form the film-forming area.

8. A method of detecting at least one property of a material in the form of a film when exposed to an energy source comprising:
    a) forming a liquid sample of said material;
    b) applying the liquid sample onto a frame comprising at least three sides with at least one of the sides being moveable, said frame defining a film-forming area without a substrate;

c) contacting the liquid with the at least one moveable side;

d) moving the at least one moveable side to draw the liquid within the film-forming area to form a film therein;

e) directing a beam from an energy source to said film; and f) analyzing the properties of the thin film based on the passage of the beam through the film.

9. The method of claim 8 comprising controlling the size of the film-forming area.

10. The method of claim 8 further comprising controlling the thickness of said thin film.

11. The method of claim 9 comprising adjusting the distance between the sides of the frame.

12. The method of claim 10 comprising rotating the frame at a sufficient rate of speed to remove excess liquid from the frame.

13. The method of claim 8 wherein the frame comprises two spaced apart sides which converge at an apex, said method comprising contacting said apex with the liquid and drawing the liquid with the moveable side from said apex.

14. The method of claim 8 comprising moving a plurality of the sides of the frame to form the film-forming area.

15. A method of analyzing a sample of a liquid material comprising:

a) applying the liquid material to a frame comprising at least three sides with at least one of the sides being moveable;

b) contacting the liquid material with said at least one moveable side, said at least one moveable side being in contact with at least two of the sides of the frame to thereby define a film-forming area;

c) moving the at least one moveable side in a manner sufficient to draw the liquid between the sides in contact with the at least one moveable side within the film-forming area without the use of a substrate to form said film in said film-forming area;

d) inserting the film in a horizontal position within an instrument for detecting properties of the film;

e) passing a beam from an energy source at least once through the film; and f) detecting properties of the film from information said received from the passing step.

16. The method of claim 15 comprising passing the beam at least twice through the film.

17. The method of claim 15 comprising deflecting the beam from the energy source by at least one mirror.

18. The method of claim 17 further comprising directing the beam of energy after passing through the film to a detection means.

\* \* \* \* \*